United States Patent [19]
Ikari et al.

[11] Patent Number: 5,221,331
[45] Date of Patent: Jun. 22, 1993

[54] AQUATIC ANTIFOULING COMPOSITION

[75] Inventors: Hirotake Ikari, Ciba; Teruyoshi Takahashi, Kawaguchi; Hiroshi Kanbara, Abiko, all of Japan

[73] Assignee: Rohm and Haas Company, Philadelphia, Pa.

[21] Appl. No.: 800,651

[22] Filed: Nov. 27, 1991

[51] Int. Cl.$^5$ .............................................. C09D 5/14
[52] U.S. Cl. ........................... 106/18.33; 504/152; 504/126; 504/121; 106/18.34; 540/541; 523/122; 424/78.09; 525/348; 514/579; 428/255; 428/365; 428/907; 427/385.5; 427/386; 427/394; 427/421; 427/430.1
[58] Field of Search .................... 106/18.33, 18.34; 71/67; 540/541; 523/122; 424/78.09; 525/348; 514/579; 428/255, 365, 907; 427/385.5, 386, 394, 421, 430.1

[56] References Cited

U.S. PATENT DOCUMENTS 2,187,719 1/1940 Williams ................................ 540/541
4,439,555 3/1984 Doi et al. ............................ 106/18.33

FOREIGN PATENT DOCUMENTS 51-049227 4/1976 Japan .................................. 106/18.33
59-053560 3/1984 Japan .................................. 106/18.33
2-127479 5/1990 Japan .................................. 106/18.33

*Primary Examiner*—Mark L. Bell
*Assistant Examiner*—Anthony J. Green
*Attorney, Agent, or Firm*—Michael B. Fein

[57] ABSTRACT

An aquatic antifouling composition characterized by containing as effective antifouling component a metal salt of hexamethylenedithiocarbamic acid represented by the formula below:

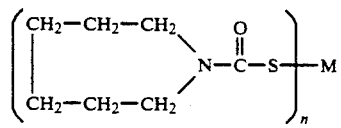

(where M is a divalent or trivalent metal; n is 2 or 3.)

9 Claims, No Drawings

AQUATIC ANTIFOULING COMPOSITION

I. BACKGROUND OF THE INVENTION

A. Field of Invention

This invention relates to an aquatic antifouling composition and a fishnet antifouling composition to be used for preventing ship-bottoms, other marine structures and fishnets such as nursery nets and stationary nets from being fouled or damaged by marine adhesive organisms.

B. Description of the Prior Art

Ships, specifically their bottoms and waterline zones, other marine structures and fishnets such as nursery nets and stationary nets are subject to adhesion and parasitism of various marine organisms: they include arthropods such as barnacles and goose barnacles, coelenterates such as hydras, annelids such as hydroides, tentacular animals such as *Bugula neritina*, mollusks such as mussels, and other collectively called animals; fine algae such as diatoms and blue-green algae, green algae such as flat green layers and see lettuces, brown algae such as *Ceramium kondoi* and Phaeophyceae, and others collectively called algae; and various kinds of bacteria called slime. Their adhesion affects the ships and so forth seriously. A great cost is required for removal of these livings and repairement or repainting of the ships, etc.

In the case of a ship, for example, a several percent increase in the resistance of its hull due to the adhesion of marine organisms causes a decrease in speed and a fall in the fuel efficiency, which would result in a serious loss.

Recently the advance of ocean development in the coastal regions has been encouraging construction and installation of large marine structures, structures, annexed thereto, and other similar structures. The structures exposed to sea water, for example, structures for harbor/facilities (such as nautical beacons, floating beacons, mooring buoys, floating piers, floating breakwaters, and floating docks), pipelines, bridges, tanks, water pipes in power stations, seaside industrial plants, mooring ships, mooring and floating fishing structures, fish preserving structures, and stationary nets and other facilities/structures for fishing, suffer various damage such as corrosion in the basal parts, sinking or loss due to the increased weight, loss of balance, etc. when the pollution-productive marine organisms have adhered and grown there.

In addition, at facilities, plants, and power stations located along seashores, when they use sea water for cooling or for the other purposes, the pollution-productive adhesive marine livings adhere to their seawater inlets and outlets, coastal structures such as channels and culverts, and growth there. The volume occupied by these livings sometimes reaches the order of some tens of percents of the inner volume of such tubular structures, which causes a decrease in the available cross-sectional area of waterways, an increase in the resistance to the liquid flow, choking of the screens to remove suspended solids, and and other damage.

Fishnets such as nursery nets and stationary nets and marine ropes are subject to adhesion of such marine organisms as barnacles, hydroides, ascidians, green algae and brown algae. Since their adhesion hinders the economic use of such nets and ropes, great labor and large expense are required for the maintenance of them.

Heretofore, for the protection of marine structures and facilities from the adhesion of harmful marine organisms sparingly soluble inorganic copper compounds, organic tin compounds, organic nitrogen-sulfur compounds and the like have been used.

These substances, however, have various drawbacks; some manifesting toxicity to men and beasts, others polluting environments, and yet others failing to maintain sufficient effect when used for a long time as an aquatic antifoulant. Organic tin compounds are highly effective in preventing the adhesion of marine organisms and they have been regarded as efficient antifouling components and widely used. Recently, however, drawbacks of these organic tin compounds—being sparingly degradable, accumulation in living bodies, toxicological problem against men and beasts, possibility to cause environmental pollution—have been drawing attention.

As antifouling components against marine organisms, tributyl tin methyacrylate copolymers, tributyl tin fluorides and other organic tin compounds are considered most desirable in terms of retention of efficacy and stability of effect. However, their safety to men and beasts, environmental pollution, etc. have become a big issue in the society.

In terms of safety to men and beasts and freedom from environmental pollution, metal salts of alkylenebisdithiocarbamic acid are rated as the most desirable antifouling components. In many cases, however, they are not satisfactory in terms of retention of efficacy and stability of effect. In order to solve these problems, a heavy metal salt of alkylenebisdithiocarbamic acid is combined with an inorganic copper compound to prepare an antifouling component, or some other antifouling components such as maleimide compounds are added to the said combination. But sufficient efficacy and stability have not yet been achieved.

Accordingly, the purpose of this invention is to provide an aquatic antifouling composition which is able to retain its effect for long periods, which is sparingly susceptible to physical or chemical deterioration when coated, which is highly safe to men and beasts, and at the same time which is least likely to cause environmental pollution.

II. SUMMARY OF INVENTION

As a result of diligent studies, the present inventors have found that an aquatic antifouling composition and a fishnet antifouling composition which contains as effective antifouling component of hexamethylenedithiocarbamic acid represented by the formula below:

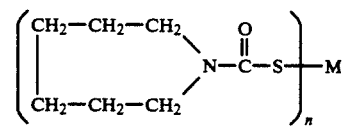

(where M is a divalent or trivalent metal; n is 2 or 3.) exhibit extremely excellent antifouling effect.

The metal salt of hexamethylenedithiocarbamic acid expressed by the above-mentioned formula is disclosed in U.S. Pat. No. 2,187,719.

As for the metal which constitutes the metal salt of hexamethylenedithiocarbamic acid of this invention, copper, zinc, manganese, iron and so forth can be cited.

The antifouling composition of this invention is prepared by mixing the compound expressed by the above-mentioned formula as an effective antifouling component with a vehicle, an organic solvent and various additives and thereby dispersing it.

In this invention, the effective antifouling component may be combined in the antifouling composition in any ratio, but preferably the ratio of the compound expressed by the above-mentioned formula should be 0.5-70 weight %. More preferably, the ratio should be 0.5-30 weight %.

The vehicle component useful in this invention is not limited, but preferably natural or process resins such as rosin, shellac and rosin ester, and synthetic resins such as alkyd resin, acrylic resin, vinyl resin, epoxy resin and rubber chloride resin are used.

Concrete examples of the solvent useful in the composition of this invention include hydrocarbons such as mineral spirits, solvent naphtha, xylene and toluene, ketones such as methyl isobutyl ketone and cyclohexanone, esters such as ethyl acetate and butyl acetate, and alcohols such as n-butanol and isopropyl alcohol. One or more kinds of these solvents may be used in mixture.

Concrete example of the additives useful in the composition of this invention include organic or inorganic coloring pigments such as titanium oxide, carbon black, cyanine blue and chrome yellow, dyes such as thiazole dye, azo dye, nitroso dye and anthraquinone dye, extenders such as talc, calcium carbonate and magnesium carbonate, anti-dripping agents, levelling agents and UV absorbents. One or more kinds of these additives may be used.

It is also possible to use the aquatic antifouling composition of this invention in combination with conventional antifoulants: for example, copper compounds such as copper (I) oxide, copper thiocyanate and copper naphthenate; 2-methylthio-4-t-2-butylamino-6-cyclopropylamino-S-triazine, 2,4,5,6-tetrachloroisophthalonitrile, N,N-dimethyldichlorophenyl urea, 4,5-dichloro-2-n-octyl-4-isothiazolin-3-one, N-(fluorodichloromethylthio)sulfamide, zinc salts of 2-pyridinethiol-1-oxide, 2,4,6-trichlorophenylmaleimide and the like. Needless to say, improvement of the antifouling effect can be expected by combining these compounds.

The antifouling composition of the present invention, when applied to ships on their bottoms, fishnets such as nursery nets, stationary nets and marine ropes, harbor facilities and structures, and oceanic structures such as pipelines and bridges, reveals excellent effect in preventing in preventing the adhesion of a wide variety of harmful organisms including animals such as barnacles, hydroides, ascidians, sea mussels and mussels; algae such as sea lettuces, flat green lavers, marine-spirogyras; various bacteria and molds collectively called slime; and seaweeds such as diatoms. And yet its effect remains for a long time.

It has been known that dithiocarbamate compounds are highly effective in controlling slime and algae but their effect is insufficient against such animals as barnacles, hydroides, sea mussels and mussels. The antifouling composition of the present invention, however, has antifouling effect against a wide variety of these animals, slime and algae.

The antifouling composition of this invention can be used in the same manner as the conventional antifouling composition are used. On ship-bottoms and marine structures, for example, the antifouling compositions of the present invention is mixed with conventional coating materials or the like, and the mixture is coated on their surface by the conventional coating method. After the surface gets dry, they can be used. In the case of ropes and fishnets, they are dipped in a fishnet dye containing the antifouling composition of this invention, withdrawn from there, and then naturally dried before use.

Now, the effect of the antifouling composition of this invention will be described more specifically below with reference to concrete examples and comparative examples. It should be noted that this invention is not limited to these concrete examples.

EXAMPLES

Concrete Examples 1 through 8 and Comparative Examples 1 through 3

Steel panels (300×100×1.6 mm) which had been given sandblast treatment were painted with an etching primer once, with an anticorrosive paint four times and finally, two times with one of the newly prepared antifouling paints of concrete Example 1 through 8 and Comparative Examples 1 through 3 shown in Table 1. Next, these panels were dried at room temperature for four days. Then they were hung from the rafts which had been located in Uragami Bay, Wakayama Prefecture, Japan. They were dipped in the sea 1.5 m below the surface. Then, the state of adhesion of marine livings was observed for 30 months. For control, some panels not treated with any antifouling paints were also dipped and observed.

For the evaluation of effect, the following scale based on the area of adhesion (%) were used. The test results are shown in Table 2.

| Scale | SCALE OF ADHESION RESULTS PERTAINING TO TABLES 2 AND 4 |
|---|---|
| | Area of adhesion with marine organisms |
| 0 | No adhesion |
| 1 | 5% or less |
| 2 | 10% or less |
| 3 | 25% or less |
| 4 | 50% or less |
| 5 | more than 50% |

Concrete Examples 9 through 16 and Comparative Examples 4 through 6

Tests for Marine-structure Antifoulants

Steel panels (300×100×2 mm) which had been given sandblast treatment were coated with an etching primer (15μ in thickness when dried) and an anticorrosive paint (200μ in thickness when dried) prior to these tests. These panels were painted with one of the newly prepared antifouling paints of Concrete Examples 9 through 16 and Comparative Examples 4 through 6 shown in Table 3 in a way that the thickness of the coating would become 100μ when dried. Next, these panels were dried at room temperature for four days. Then, they were hung from the rafts which had been located in Uragami Bay, Wakayama Prefecture. They were dipped in the sea 1.5 m below the surface. Then, the state of adhesion of marine livings was observed for 36 months. For control, some panels not treated with any antifouling paint were also dipped and observed. The evaluation of effect was conducted in the same way as mentioned in the Concrete Example 1. The test results are shown in Table 4.

TABLE 1

| Components | Examples Concrete Example 1 | 2 | 3 | 4 | 5 | 6 | 7 | 8 | Comparative Ex. 1 | 2 | 3 |
|---|---|---|---|---|---|---|---|---|---|---|---|
| Copper salt of hexamethylenedithiocarbamic acid | 10 | | | 20 | | | 10 | | | | |
| Zinc salt of hexamethylenedithiocarbamic acid | | 10 | | | 20 | | | 20 | | | |
| Manganese salt of hexamethylenedithiocarbamic acid | | | 10 | | | 20 | | | | | |
| Manganese salt of ethylenebisdithiocarbamic acid | | | | | | | | | | | 15 |
| Copper (I) oxide | | | | | | | | | 30 | | |
| Tributyl tin fluoride (Nitto Kasei/Tributon F) | | | | | | | | | | 15 | |
| Vinyl acetate-vinyl chloride copolymer/VYHH | 6 | 6 | 6 | 6 | 6 | 6 | | | 6 | 6 | 6 |
| Rubber chloride (Good Year/Priolight S-5B) | | | | | | | 9 | 9 | | | |
| WW Rosin | 6 | 6 | 6 | 6 | 6 | 6 | 10 | 10 | 6 | 6 | 6 |
| Tricresyl phosphate | 2 | 2 | 2 | 2 | 2 | 2 | | | 2 | 2 | 2 |
| Paraffin chloride | | | | | | | 4 | 4 | | | |
| Magnesium oxide | | | | | | | 10 | 6 | | | |
| China clay | | | | | | | 10 | 8 | | | |
| Barium sulfate (of sedimenting property) | 15 | 15 | 15 | 10 | 10 | 10 | | | 10 | 15 | 15 |
| Talc | 15 | 15 | 15 | 10 | 10 | 10 | | | 8 | 15 | 15 |
| Iron oxide red | 10 | 10 | 10 | 10 | 10 | 10 | 10 | 6 | 7 | 10 | 10 |
| Anti-dripping agent (Itoh Oil Refinery/ASA-D-120) | 1 | 1 | 1 | 1 | 1 | 1 | 1 | 1 | 1 | 1 | 1 |
| Thixotropic | | | | | | | 1 | 1 | | | |
| Methyl isobutyl ketone | 20 | 20 | 20 | 20 | 20 | 20 | | | 20 | 20 | 20 |
| Xylol | 15 | 15 | 15 | 15 | 15 | 15 | | | 10 | 10 | 10 |
| Solvent naphtha | | | | | | | 35 | 35 | | | |

TABLE 2

| No. of Months passed | Evaluation of Area adhered by Marine Organisms | | | | | |
|---|---|---|---|---|---|---|
| | 3 | 6 | 12 | 18 | 24 | 30 |
| Concrete Example | | | | | | |
| 1 | 0 | 0 | 0 | 0 | 1 | 1 |
| 2 | 0 | 0 | 0 | 0 | 1 | 1 |
| 3 | 0 | 0 | 0 | 0 | 1 | 1 |
| 4 | 0 | 0 | 0 | 0 | 0 | 1 |
| 5 | 0 | 0 | 0 | 0 | 0 | 1 |
| 6 | 0 | 0 | 0 | 0 | 0 | 1 |
| 7 | 0 | 0 | 0 | 0 | 1 | 1 |
| 8 | 0 | 0 | 0 | 0 | 0 | 1 |
| Comparative Example | | | | | | |
| 1 | 0 | 0 | 1 | 2 | 3 | 4 |
| 2 | 0 | 0 | 0 | 1 | 2 | 3 |
| 3 | 0 | 0 | 1 | 2 | 3 | 4 |
| No Treatment | 5 | 5 | 5 | 5 | 5 | 5 |

TABLE 4

| No. of Months passed | Evaluation of Area adhered by Marine Organisms | | | | | | |
|---|---|---|---|---|---|---|---|
| | 3 | 6 | 12 | 18 | 24 | 30 | 36 |
| Concrete Example | | | | | | | |
| 9 | 0 | 0 | 0 | 0 | 0 | 1 | 2 |
| 10 | 0 | 0 | 0 | 0 | 0 | 1 | 2 |
| 11 | 0 | 0 | 0 | 0 | 0 | 1 | 2 |
| 12 | 0 | 0 | 0 | 0 | 0 | 0 | 1 |
| 13 | 0 | 0 | 0 | 0 | 0 | 0 | 1 |
| 14 | 0 | 0 | 0 | 0 | 0 | 0 | 1 |
| 15 | 0 | 0 | 0 | 0 | 0 | 1 | 2 |
| 16 | 0 | 0 | 0 | 0 | 0 | 0 | 1 |
| Comparative Example | | | | | | | |
| 4 | 0 | 0 | 0 | 1 | 2 | 3 | 4 |
| 5 | 0 | 0 | 0 | 1 | 2 | 3 | 5 |
| 6 | 0 | 0 | 0 | 0 | 1 | 2 | 4 |
| No Treatment | 5 | 5 | 5 | 5 | 5 | 5 | 5 |

TABLE 3

| Components | Examples Concrete Example 9 | 10 | 11 | 12 | 13 | 14 | 15 | 16 | Comparative Ex. 4 | 5 | 6 |
|---|---|---|---|---|---|---|---|---|---|---|---|
| Copper salt of hexamethylenedithiocarbamic acid | 15 | | | 25 | | | 15 | | | | |
| Iron salt of hexamethylenedithiocarbamic acid | | 15 | | | 25 | | | | | | |
| Manganese salt of hexamethylenedithiocarbamic acid | | | 15 | | | 25 | | 25 | | | |
| Manganese salt of ethylenebisdithiocarbamic acid | | | | | | | | | 20 | | |
| Copper (I) oxide | | | | | | | | | | 35 | |
| Tributyl tin fluoride (Nitto Kasei/Tributon F) | | | | | | | | | | | 20 |
| Vinyl acetate-vinyl chloride copolymer/VYHH | 6 | 6 | 6 | 6 | 6 | 6 | | | 6 | 6 | 6 |
| Rubber chloride (Good Year/Priolight S-5B) | | | | | | | 9 | 9 | | | |
| WW Rosin | 6 | 6 | 6 | 6 | 6 | 6 | 10 | 10 | 6 | 6 | 6 |
| Tricresyl phosphate | 2 | 2 | 2 | 2 | 2 | 2 | | | 2 | 2 | 2 |
| Paraffin chloride | | | | | | | 3 | 3 | | | |
| Magnesium oxide | | | | | | | 9 | 5 | | | |
| China clay | | | | | | | 9 | 6 | | | |
| Barium sulfate (of sedimenting property) | 13 | 13 | 13 | 9 | 9 | 9 | | | 10 | 5 | 10 |
| Talc | 13 | 13 | 13 | 9 | 9 | 9 | | | 10 | 5 | 10 |
| Iron oxide red | 9 | 9 | 9 | 7 | 7 | 7 | 8 | 5 | 10 | 5 | 10 |
| Anti-dripping agent (Itoh Oil Refinery/ASA-D-120) | 1 | 1 | 1 | 1 | 1 | 1 | 1 | 1 | 1 | 1 | 1 |
| Thixotropic | | | | | | | 1 | 1 | | | |
| Methyl isobutyl ketone | 20 | 20 | 20 | 20 | 20 | 20 | | | 20 | 20 | 20 |
| Xylol | 15 | 15 | 15 | 15 | 15 | 15 | | | 15 | 15 | 15 |
| Solvent naphtha | | | | | | | 35 | 35 | | | |

Concrete Examples 17 through 22 and Comparative Examples 7 through 9

Tests for Fishnet Antifoulants

Polyethylene knotless net (5 knots 400 denier/70 pieces) was dipped in the fishnet antifoulants of Concrete Examples 17 shown in Table 5. After natural drying, the net was hung from rafts which had been located at about 2 km offshore in Uragami Bay, Katsuura, Wakayama Prefecture, and dipped in the sea 1.5 m below the surface. Then, the state of adhesion of marine organisms was observed and recorded for 6 months. For control, a piece of net not treated with any antifoulant was also tested. Table 6 shows the test results.

Scale for Evaluation

A: No adhesion of marine organisms
B: Some adhesion is observed, but the net can stand continuous use.
C: Marine organisms are adhering in fairly large volumes, and the net is unfit for continuous use.
D: Enormous volumes of marine organisms are adhering.

TABLE 5

| Components | Concrete Example | | | | | | Comparative Ex. | | |
|---|---|---|---|---|---|---|---|---|---|
| | 17 | 18 | 19 | 20 | 21 | 22 | 7 | 8 | 9 |
| Copper salt of hexamethylenedithiocarbamic acid | 10 | | | 20 | | | | | |
| Zinc salt of hexamethylenedithiocarbamic acid | | 10 | | | 20 | | | | |
| Manganese salt of hexamethylenedithiocarbamic acid | | | 10 | | | 20 | | | |
| Tetramethyl thiruram disulfide | | | | | | | 15 | | |
| Bisdimethyldithiocarbamoyl zinc ethylenebisdithiocarbamate | | | | | | | | 15 | |
| Tributyl tin fluoride (Nitto Kasei/Tributon F) | | | | | | | | | 15 |
| Acrylic resin (50% xylene solution) | 15 | 15 | 15 | 15 | 15 | 15 | 15 | 15 | 15 |
| Rubber chloride (Good Year/Priolight S-5B) | | | | | | | | | |
| WW Rosin | | | | | | | | | |
| Ethylene-vinyl acetate copolymer resin | | | | | | | | | |
| Xylene | 75 | 75 | 75 | 65 | 65 | 65 | 70 | 70 | 70 |
| Solvent naphtha | | | | | | | | | |
| Methyl ethyl ketone | | | | | | | | | |

TABLE 6

| No. of Months passed | Evaluation of Area adhered by Marine Organisms | | | | | |
|---|---|---|---|---|---|---|
| | 1 | 2 | 3 | 4 | 5 | 6 |
| Concrete Example | | | | | | |
| 17 | A | A | A | A | B | B |
| 18 | A | A | A | B | B | B |
| 19 | A | A | A | A | B | B |
| 20 | A | A | A | A | A | B |
| 21 | A | A | A | A | B | B |
| 22 | A | A | A | A | B | B |
| Comparative Example | | | | | | |
| 7 | C | D | | | | |
| 8 | A | A | B | B | C | D |
| 9 | A | A | B | B | C | D |
| No Treatment | D | D | — | — | — | — |

EFFECT OF THE INVENTION

The aquatic antifouling composition of this invention retains excellent effect for a long time compared to the conventional antifouling compositions. And yet it is highly safe to men and beasts. According to this invention, the possibility to cause environmental pollution has been remarkably reduced.

Although specific embodiments and examples have been described herein, it should be born in mind that these have been provided by way of explanation and illustration and that the present invention is not limited thereby. Modifications which are within the ordinary skill in the art to make are considered to lie within the scope of the invention as defined by the following claims, including all equivalents.

We claim:

1. An aquatic antifouling composition comprising a vehicle, solvent, and additives characterized by containing as effective antifouling component a metal salt of hexamethylenedithiocarbamic acid represented by the formula below:

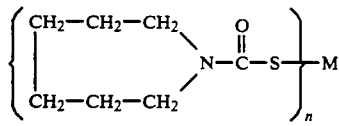

(where M is a divalent or trivalent metal; n is 2 or 3.)

2. Composition according to claim 1 wherein said salt comprises about 0.5 to 70% by weight and the balance comprises said vehicle, solvent, and additives.

3. A fishnet antifouling composition comprising a vehicle, solvent, and additives characterized by containing as an effective antifouling component a metal salt of hexamethylenedithiocarbamic acid represented by the formula below:

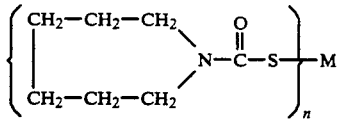

(where M is a divalent or trivalent metal; n is 2 or 3.)

4. Article comprising a marine structure coated or impregnated with a composition according to claim 1 which is characterized by resistance to fouling by marine organisms, said marine structure being selected from the group consisting of nets, ropes, harbor structures, pipelines, and bridges which are to be exposed to waters containing marine organisms.

5. Composition according to claim 1 where said vehicle is selected from the group consisting of natural resins selected from rosin, shellac and rosin ester, and synthetic resins selected from alkyd resin, acrylic resin, vinyl resin, epoxy resin and rubber chloride resin.

6. Composition according to claim 1 wherein said solvent is selected from the group consisting of hydrocarbons, ketones, esters, and alcohols.

7. Composition according to claim 1 wherein said additive is selected from the group consisting of titanium oxide, carbon black, cyanine blue, chrome yellow dyes, extenders, anti-dripping agents, levelling agents, and UV absorbents.

8. Composition according to claim 1 further including additional antifoulant selected from the group consisting of copper compounds; 2-methylthio-4-t-2-butylamino-6-cyclopropylamino-s-triazine; 2,4,5,6-tetrachloroisophthalonitrile; N,N-dimethyldichlorophenyl urea; 4,5-dichloro 2-n-octyl-4-isothiazoline-3-one; N-(fluorodichloromethylthio)sulfamide; zinc salts of 2-pyridinethiol-1-oxide; and 2,4,6-trichlorophenylmaleimide.

9. Method of protecting a marine structure comprising dipping, coating, or impregnating said structure with an aquatic antifouling composition according to claim 1.

* * * * *